United States Patent [19]

Kashiba

[11] Patent Number: 6,114,162
[45] Date of Patent: *Sep. 5, 2000

[54] ATMOSPHERE REGULATOR AND METHOD FOR CULTURING ANAEROBIC BACTERIA

[75] Inventor: Takashi Kashiba, Kanagawa-ken, Japan

[73] Assignee: Mitsubishi Gas Chemical Company, Inc., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/050,624

[22] Filed: Mar. 30, 1998

[30] Foreign Application Priority Data

Apr. 1, 1997 [JP] Japan ................................ 9-082738

[51] Int. Cl.⁷ .............................. C12N 1/20; C12Q 1/02; C12M 1/00
[52] U.S. Cl. ................... 435/252.1; 435/29; 435/283.1
[58] Field of Search .................. 435/29, 252.1, 435/283.1

[56] References Cited

U.S. PATENT DOCUMENTS

| | | | |
|---|---|---|---|
| 4,337,276 | 6/1982 | Nakamura et al. | 426/124 |
| 4,588,561 | 5/1986 | Aswell et al. | 422/238 |
| 4,605,617 | 8/1986 | Kasugai | 435/29 |
| 5,034,331 | 7/1991 | Brewer | 435/298 |

FOREIGN PATENT DOCUMENTS

| | | |
|---|---|---|
| 0 111 583 | 6/1984 | European Pat. Off. . |
| 0 120 111 | 10/1984 | European Pat. Off. . |
| 0 527 228 | 2/1993 | European Pat. Off. . |
| 0 798 373 | 10/1997 | European Pat. Off. . |
| 59-98686 | 6/1984 | Japan . |
| 1-202281 | 8/1989 | Japan . |

OTHER PUBLICATIONS

Database WPI, Section Ch, Week 7939, Derwent Publications Ltd., London, GB, AN 79–70799B of JP 54 105288 A (Aug. 18, 1979).
Database WPI, Section Ch, Week 8339, Derwent Publications ltd., London, GB, AN 83–774553 of JP 58 141780 A (Aug. 23, 1983).
Database WPI, Section Ch, Week 8226, Derwent Publications Ltd., London, GB, AN 82–53058E of JP 57 079869 (May 19, 1982).
Patent Abstracts of Japan, vol. 013, No. 227 (C–600), May 25, 1989, of JP 01 038139 A (Feb. 8, 1989).

*Primary Examiner*—Sandra E. Saucier
*Assistant Examiner*—Vera Afremova
*Attorney, Agent, or Firm*—Frishauf, Holtz, Goodman, Langer & Chick, P.C.

[57] ABSTRACT

An atmosphere regulator which comprises 100 parts by weight an oxygen absorber comprising an ascorbic acid compound, a metallic salt, water and an activated carbon, and 5 to 20 parts by weight of an alkaline earth metal hydroxide. The atmosphere regulator has a pH, as measured in accordance with JIS K1474, of 10 to 12.5. The atmosphere regulator can promptly change the atmosphere in a system into an anaerobic state and has a function for stably generating a carbon dioxide gas. The atmosphere regulator does not bring about any deterioration of performance, even when stored for a long period of time, and is compact for good receivability. Anaerobic bacteria can be cultured by the use of the atmosphere regulator.

13 Claims, No Drawings

6,114,162

ATMOSPHERE REGULATOR AND METHOD FOR CULTURING ANAEROBIC BACTERIA

BACKGROUND OF THE INVENTION

1. Field of the Invention

The present invention relates to an atmosphere regulator and a method for culturing anaerobic bacteria. More specifically, it relates to an atmosphere regulator and an atmosphere regulator package which can regulate the concentration of a carbon dioxide gas, is excellent in oxygen absorption performance, does not bring about any deterioration of the performance even when stored for a long period of time, and is compact for putting into a package, and a method for culturing anaerobic bacteria by the use of this atmosphere regulator or this package.

2. Description of the Related Art

In recent years, it has been considered as a useful means for the inspection of bacteria that various anaerobic bacteria are cultured to detect their presence, and many techniques have been developed. In particular, it has been required to make an atmosphere suitable for the culture of the anaerobic bacteria in a simple manner, and various kinds of atmosphere regulators have been suggested. For example, as the atmosphere regulator for the culture of the anaerobic bacteria which contains an ascorbic acid compound, there has been disclosed an atmosphere regulator which can give an anaerobic state and a predetermined carbon dioxide gas concentration within 6 hours in Japanese Patent Application Laid-open Nos. 51890/1983 and 98686/1984. However, in order to regulate the atmosphere, a long time is taken, and so there is a problem that the accuracy of the bacteria inspection is impaired. In addition, Japanese Patent Application Laid-open No. 105288/1979 has disclosed a method for culturing anaerobic bacteria by the use of an atmosphere regulator mainly comprising an ascorbic acid compound and including two or more alkali compounds, but this method has a problem that the regulation of a pH is insufficient under the influence of a contained carbonate or hydrogencarbonate and a storage stability is poor.

Furthermore, in Japanese Patent Application Laid-open No. 202281/1989, there is disclosed an atmosphere regulator which comprises an ascorbic acid compound as a main component, an alkali hydroxide, an activated carbon, a ferrous salt, water and calcium silicate, but the mixture becomes unequal under the influence of the size of the alkali hydroxide to cause the scattering of a carbon dioxide gas concentration. In addition, an oxygen absorbing reaction is impaired by the influence of contained calcium silicate, so that the size of an package including the atmosphere regulator tends to increase.

SUMMARY OF THE INVENTION

The present invention has been developed to solve the above-mentioned problems of conventional techniques, and an object of the present invention is to provide an atmosphere regulator which can promptly change the atmosphere in a system into an anaerobic state, has a function for stably generating a carbon dioxide gas, does not bring about any deterioration of a performance even when stored for a long period of time, and is compact for putting into a package, and a method for culturing anaerobic bacteria by the use of this atmosphere regulator.

DETAILED DESCRIPTION OF THE INVENTION

The first aspect of the present invention is directed to an atmosphere regulator which comprises 100 parts by weight of an oxygen absorber comprising an ascorbic acid compound, a metallic salt, water and an activated carbon, and 5 to 20 parts by weight of an alkaline earth metal hydroxide, a pH of the atmosphere regulator (as measured in accordance with JIS K1474) being in the range of 10 to 12.5.

The second aspect of the present invention is directed to an atmosphere regulator wherein the oxygen absorber comprises a powder obtained by impregnating the activated carbon having an average particle diameter of 0.1 to 2 mm with the ascorbic acid compound, the metallic salt and water.

The third aspect of the present invention is directed to an atmosphere regulator wherein the alkaline earth metal hydroxide comprises a powder having an average particle diameter of 1 to 100 $\mu$m.

The fourth aspect of the present invention is directed to an atmosphere regulator package which is made by wrapping the above-mentioned atmosphere regulator into a breathable package material.

The fifth aspect of the present invention is directed to a method for culturing anaerobic bacteria which comprises the steps of placing this atmosphere regulator or this atmosphere regulator package in a hermetically sealable container together with a culture medium inoculated with the anaerobic bacteria, and then hermetically sealing the container to regulate concentrations in the container atmosphere so that an oxygen concentration may be 0.1% or less and a carbon dioxide gas concentration may be in the range of 9 to 12% within 3 hours from the sealing.

Next, the present invention will be described in more detail.

In the present invention, examples of a usable ascorbic acid compound include L-ascorbic acid, sodium L-ascorbate, calcium L-ascorbate and sodium D-isoascorbate, and they may be used singly or in the form of a mixture thereof. It is preferable that the ascorbic acid compound, when used, is dissolved in water, and with the resultant aqueous solution, an activated carbon is then impregnated. In the case that the activated carbon is impregnated with the aqueous ascorbic acid compound solution, the aqueous solution of the ascorbic acid compound preferably has a high concentration, because the amount of the activated carbon to be used can be reduced. Hence, the use of the saturated aqueous solution of the ascorbic acid compound is preferable. Concretely, it is particularly preferable to use sodium L-ascorbate.

The amount of the ascorbic acid compound is suitably decided, but it is preferably in the range of 20 to 200 parts by weight, more preferably 50 to 150 parts by weight with respect to 100 parts by weight of the activated carbon.

As the activated carbon in the present invention, there can be used an activated carbon prepared from a raw material such as a sawdust, a coal or coconut shells in a suitable manner such as a steam activation, a chemical activation or a carbon dioxide gas activation. A method in which the activated carbon is impregnated with an aqueous solution of the ascorbic acid compound and the metallic salt is effective in that the absorption of oxygen and the generation of the carbon dioxide gas by the atmosphere regulator can reproducibly be accomplished and the atmosphere regulator can also be compacted.

The particle diameter of the activated carbon is preferably in the range of 0.1 to 2 mm, more preferably 0.2 to 1 mm. If the particle diameter of the activated carbon is too small, the flowability of the atmosphere regulator is poor, so that the automatic filling of the atmosphere regulator into a breathable package is difficult. On the other hand, if the particle diameter of the activated carbon is too large, an oxygen absorption performance deteriorates, and there might occur a problem that the atmosphere regulator break the package and the contents in the package spill out.

Examples of the preferable metallic compounds in the present invention include anhydrous salts and water-containing salts of ferrous chloride, ferric chloride, ferric sulfate, ferrous sulfate, manganese chloride, zinc sulfate, copper sulfate and copper chloride, and above all, ferrous sulfate and its water-containing salt are particularly preferable.

The amount of the metallic salt is preferably in the range of 5 to 20 parts by weight with respect to 100 parts by weight of the ascorbic acid compound, depending on a kind of metallic salt. In this case, it is not preferable to add a carbonate or a hydrogencarbonate, because the generation amount of the carbon dioxide gas cannot be controlled and the atmosphere regulator having a reproducible quality cannot be obtained on occasion.

As an alkaline earth metal hydroxide in the present invention, various kinds of hydroxides can be used, but calcium hydroxide, magnesium hydroxide and mixtures thereof are preferable.

The alkaline earth metal hydroxide is preferably in the state of a powder having an average particle diameter of 1 to 100 $\mu$m, more preferably 2 to 50 $\mu$m. If the particle diameter is too small, the handling of the powder is difficult, and if it is too large, the powder cannot uniformly be mixed with activated carbon, with the result that it is difficult to industrially produce the atmosphere regulator having a reproducible quality.

The amount of the alkaline earth metal hydroxide to be blended is required to be in the range of 5 to 20 parts by weight with respect to 100 parts by weight of an oxygen absorber in which the activated carbon is impregnated with the ascorbic acid, the metallic salt and water. If the amount of the alkalined earth metal hydroxide is less than the above-mentioned range, the absorption of oxygen and the generation of the carbon dioxide gas cannot promptly be carried out. On the other hand, if it is more than the above-mentioned range, the generation amount of the carbon dioxide gas is insufficient, so that a gas atmosphere suitable for the culture of anaerobic bacteria cannot be given.

The pH of the atmosphere regulator depends on the pH of the activated carbon as well as kinds and blend ratios of components such as the metallic salt and the alkaline earth metal hydroxide, but it is necessary that the respective additives should be mixed in the above-mentioned preferable ranges so that the pH of the finally obtained atmosphere regulator may be in the range of 10 to 12.5 (as measured in accordance with the measurement way of JIS K1474). If the pH of the atmosphere regulator is less than 10, an oxygen absorbing reaction and a carbon dioxide gas generating function cannot promptly be carried out, and in addition, the generation of the carbon dioxide gas during the storage of the atmosphere regulator cannot be inhibited. On the other hand, if the pH is more than 12.5, the ascorbic acid compound which is the main component decomposes during the storage, so that the deterioration of the performance occurs, which makes it difficult to obtain the atmosphere gas suitable for the culture of the anaerobic bacteria.

A breathable package material which is used to make the atmosphere regulator package by wrapping the atmosphere regulator in the present invention must be a material through which oxygen and the carbon dioxide gas can permeate, and preferable is the material having an oxygen permeability of 300 cc/HR.cr$^2$ or more and a carbon dioxide gas permeability of 300 cc/HR.cm$^2$ or more. As the breathable package material, a known breathable package material can be used, and its examples include nonwoven fabrics of synthetic fibers, synthetic papers, microporous films, papers and composite package materials of these materials on which a perforated polyethylene, a synthetic fiber net or the like is stuck as a reinforcing material.

The atmosphere regulator or the atmosphere regulator package can be placed in a hermetically sealable container together with a culture medium inoculated with the anaerobic bacteria, followed by hermetically sealing the container, whereby the concentrations of the respective components in the container atmosphere can be regulated so that an oxygen concentration may be 0.1% or less and a carbon dioxide gas concentration may be in the range of 9 to 12% within 3 hours from the sealing. That is to say, according to the present invention, there can be provided a method for simply and accurately culturing the anaerobic bacteria.

The atmosphere regulator according to the present invention is an atmosphere regulator which comprises 100 parts by weight of an oxygen absorber comprising an ascorbic acid compound, a metallic salt, water and an activated carbon, and 5 to 20 parts by weight of an alkaline earth metal hydroxide, a pH of the atmosphere regulator (as measured in accordance with JIS K1474) being in the range of 10 to 12.5, and this atmosphere regulator is excellent in an oxygen absorption performance and a carbon dioxide gas generating function, can stably maintain the function even when stored for a long period of time, and is compact for a good receivability.

When the atmosphere regulator of the present invention is used, the gas concentrations in the atmosphere can be regulated so that an oxygen concentration may be 0.1% or less and a carbon dioxide gas concentration may be in the range of 9 to 12% within 3 hours, so that the anaerobic bacteria can suitably be cultured.

Next, the present invention will be described in more detail in accordance with examples, but the scope of the present invention should not be limited to these examples at all.

EXAMPLE 1

4 kg of activated carbon particles having an average particle diameter of 0.5 mm (maximum diameter=0.9 mm) was placed in a 30 liter nauta mixer, and a solution prepared by dissolving 0.6 kg of ferrous sulfate heptahydrate in 10 kg of an aqueous 45% sodium ascorbate solution was then poured into the mixer to impregnate the activated carbon with the solution. Afterward, 2.0 kg of a magnesium hydroxide powder having an average particle diameter of 20 $\mu$m (maximum diameter=50 $\mu$m) was put therein, followed by mixing. The thus obtained mixture was then discharged into gas barrier bags (a polyvinylidene chloride-coated nylon-polyethylene-laminated film) in an amount of 2 kg/bag to obtain 8 bags numbered in the order of the discharge. The fluidity of the powder was good, and the discharge was done without any problem. From each of the first, fifth and eighth bags in the order of the discharge, 20 g of a sample was taken, and each sample was then filled into a bag (size=100 mm×140 mm) made of a paper inside which a perforated polyethylene film was laminated (oxygen permeability= 2000 cc/HR.cm$^2$), followed by heat sealing, thereby preparing the packages each including the atmosphere regulator sample.

Each of the thus prepared packages was received in a bag of a polyvinylidene chloride-coated nylon-polyethylene laminate film (size=400×220 mm) together with 2.5 liters of air, and then hermetically sealed. Next, the thus sealed bags were stored in a thermostatic chamber at 37° C. to measure a change with time of the composition of a gas in each bag. The results are shown in Table 1.

TABLE 1

|  | Concentration (%) | 1 hour | 2 hours | 3 hours | 24 hours |
| --- | --- | --- | --- | --- | --- |
| First Bag | Oxygen | 0.1 or less | 0.1 or less | 0.1 or less | 0.1 or less |
|  | Carbon Dioxide Gas | 9.8 | 10.2 | 10.8 | 10.0 |
| Fifth Bag | Oxygen | 0.1 or less | 0.1 or less | 0.1 or less | 0.1 or less |
|  | Carbon Dioxide Gas | 9.8 | 10.7 | 10.9 | 10.1 |
| Eighth Bag | Oxygen | 0.1 or less | 0.1 or less | 0.1 or less | 0.1 or less |
|  | Carbon Dioxide Gas | 9.8 | 10.4 | 10.9 | 10.0 |

EXAMPLE 2

An experiment was conducted by the same procedure as in Example 1 except that 2.0 kg of a magnesium oxide powder having an average particle diameter of 20 μm (maximum diameter=50 μm) was replaced with 2.0 kg of a calcium oxide powder having an average particle diameter of 20 μm (maximum diameter=50 μm). The results are shown in Table 2.

TABLE 2

|  | Concentration (%) | 1 hour | 2 hours | 3 hours | 24 hours |
| --- | --- | --- | --- | --- | --- |
| First Bag | Oxygen | 0.1 or less | 0.1 or less | 0.1 or less | 0.1 or less |
|  | Carbon Dioxide Gas | 8.8 | 9.2 | 9.8 | 10.0 |
| Fifth Bag | Oxygen | 0.1 or less | 0.1 or less | 0.1 or less | 0.1 or less |
|  | Carbon Dioxide Gas | 8.7 | 8.7 | 9.9 | 10.4 |
| Eighth Bag | Oxygen | 0.1 or less | 0.1 or less | 0.1 or less | 0.1 or less |
|  | Carbon Dioxide Gas | 8.6 | 9.4 | 9.2 | 10.5 |

Comparative Example 1

An experiment was conducted by the same procedure as in Example 1 except that 2.0 kg of a magnesium oxide powder having an average particle diameter of 20 μm (maximum diameter=50 μm) was replaced with 2.0 kg of calcium oxide particles having an average particle diameter of 0.8 mm (maximum diameter=1.2 mm). The results are shown in Table 3.

TABLE 3

|  | Concentration (%) | 1 hour | 2 hours | 3 hours | 24 hours |
| --- | --- | --- | --- | --- | --- |
| First Bag | Oxygen | 0.52 | 0.21 | 0.1 or less | 0.1 or less |
|  | Carbon Dioxide Gas | 6.8 | 7.2 | 6.8 | 9.0 |
| Fifth Bag | Oxygen | 0.26 | 0.1 or less | 0.1 or less | 0.1 or less |
|  | Carbon Dioxide Gas | 9.9 | 9.7 | 9.9 | 10.8 |
| Eighth Bag | Oxygen | 1.1 | 0.45 | 0.15 | 0.1 or less |
|  | Carbon Dioxide Gas | 13.8 | 15.4 | 15.9 | 13.2 |

Comparative Example 2

An experiment was conducted by the same procedure as in Example 2 except that calcium hydroxide was used in an amount of 5.0 kg. The results are shown in Table 4.

TABLE 4

|  | Concentration (%) | 1 hour | 2 hours | 3 hours | 24 hours |
| --- | --- | --- | --- | --- | --- |
| First Bag | Oxygen | 0.1 or less | 0.1 or less | 0.1 or less | 0.1 or less |
|  | Carbon Dioxide Gas | 4.8 | 5.2 | 5.4 | 4.2 |
| Fifth Bag | Oxygen | 0.1 or less | 0.1 or less | 0.1 or less | 0.1 or less |
|  | Carbon Dioxide Gas | 4.6 | 4.5 | 4.8 | 4.0 |
| Eighth Bag | Oxygen | 0.1 or less | 0.1 or less | 0.1 or less | 0.1 or less |
|  | Carbon Dioxide Gas | 4.8 | 4.5 | 4.8 | 3.7 |

Comparative Example 3

An experiment was conducted by the same procedure as in Example 1 except that a sodium hydrogencarbonate powder having an average particle diameter of 35 μm (maximum diameter=50 μm) was further added as an alkali component. The results are shown in Table 5.

TABLE 5

|  | Concentration (%) | 1 hour | 2 hours | 3 hours | 24 hours |
| --- | --- | --- | --- | --- | --- |
| First Bag | Oxygen | 1.1 | 0.23 | 0.1 or less | 0.1 or less |
|  | Carbon Dioxide Gas | 8.8 | 9.2 | 12.8 | 15.2 |
| Fifth Bag | Oxygen | 0.8 | 0.1 or less | 0.1 or less | 0.1 or less |
|  | Carbon Dioxide Gas | 8.6 | 9.5 | 12.0 | 16.5 |

TABLE 5-continued

| | Concentration (%) | 1 hour | 2 hours | 3 hours | 24 hours |
|---|---|---|---|---|---|
| Eighth Bag | Oxygen | 0.8 | 0.56 | 0.1 or less | 0.1 or less |
| | Carbon Dioxide Gas | 8.2 | 9.3 | 12.4 | 15.7 |

Comparative Example 4

The preparation of an atmosphere regulator was tried by the same procedure as in Example 1 except that in place of 4 kg of activated carbon particles having an average particle diameter of 0.5 mm (maximum diameter=0.9 mm), a mixture of 2 kg of a calcium silicate powder having an average particle diameter of 50 µm and 2 kg of activated carbon particles having an average particle diameter of 0.5 mm (maximum diameter=0.9 mm) was placed in a 30 liter nauta mixer. However, the powder was not sufficiently impregnated with an aqueous solution of sodium ascorbate and ferrous sulfate heptahydrate, so that the mixture was in a muddy state, which made its discharge impossible.

Comparative Example 5

An experiment was conducted by the same procedure as in Example 1 except that 2 kg of a calcium silicate powder having an average particle diameter of 50 µm was further added as an adsorbent component. The results are shown in Table 6.

TABLE 6

| | Concentration (%) | 1 hour | 2 hours | 3 hours | 24 hours |
|---|---|---|---|---|---|
| First Bag | Oxygen | 4.3 | 1.53 | 0.2 | 0.1 or less |
| | Carbon Dioxide Gas | 6.5 | 8.8 | 9.8 | 10.5 |
| Fifth Bag | Oxygen | 4.1 | 2.1 | 0.5 | 0.1 or less |
| | Carbon Dioxide Gas | 5.8 | 7.5 | 8.6 | 10.5 |
| Eighth Bag | Oxygen | 4.6 | 1.8 | 0.15 | 0.1 or less |
| | Carbon Dioxide Gas | 6.0 | 8.0 | 9.2 | 10.3 |

EXAMPLE 3

The pHs of the atmosphere regulators in Example 1 were measured (in accordance with JIS K1474), and as a result, the first, fifth and eighth bags all had a pH of 10.6. A sample was taken out of the fifth bag, and a package including the atmosphere regulator was prepared in the same manner as in Example 1 and then put in a bag made of an aluminum foil-laminated polyethylene film, followed by hermetic sealing (an air amount in the bag=10 cc or less). This sealed bag was stored at 35° C. for 3 months. After the storage, the aluminum-laminated film bag was opened, and the package was taken out and then put in a bag (size=400×220 mm) of a polyvinylidene chloride-coated nylon-polyethylene-laminated film together with 2.5 liters of air, followed by hermetic sealing. Next, this sealed bag was stored in a thermostatic chamber at 37° C. to measure a change with time of the composition of a gas in each bag. The results are shown in Table 7.

Comparative Example 6

The pHs of the atmosphere regulators in Comparative Example 2 were measured (in accordance with JIS K1474), and as a result, the first, fifth and eighth bags all had a pH of 12.8. A sample was taken out of the fifth bag, and a package including the atmosphere regulator was then prepared. Afterward, a storage test was made in the same manner as in Example 3. The results are shown in Table 7.

TABLE 7

| | Concentration (%) | 1 hour | 2 hours | 3 hours | 24 hours |
|---|---|---|---|---|---|
| Example 3 | Oxygen | 0.1 or less | 0.1 or less | 0.1 or less | 0.1 or less |
| | Carbon Dioxide Gas | 9.9 | 10.1 | 10.5 | 10.2 |
| Comp. Example 6 | Oxygen | 2.1 | 0.15 | 0.1 or less | 0.1 or less |
| | Carbon Dioxide Gas | 4.3 | 4.1 | 4.3 | 5.0 |

Comparative Example 7

The pHs of the atmosphere regulators in Comparative Example 3 were measured (in accordance with JIS K1474), and as a result, the first and fifth bags both had a pH of 8.4 and the eighth bag had a pH of 8.3. A sample was taken out of the fifth bag, and a package including the atmosphere regulator was then prepared. Afterward, a storage test was made in the same manner as in Example 3. However, a carbon dioxide gas was generated from the storage sample, and at the fifth day of the storage, an aluminum foil-laminated film bag was broken. Thus, the test was interrupted.

In Comparative Example 1 in which the calcium hydroxide particles were used, the contact of the ascorbic acid compound as the main component with calcium hydroxide was insufficient, so that an oxygen absorbing performance was poor, and the mixture became unequal during the mixing of a powder, and it gave rise to the result that the generation of the carbon dioxide gas was uneven. As in Comparative Examples 2 and 6, in the case that the amount of calcium hydroxide was too large, the oxygen absorption performance was good, but the generation of the carbon dioxide gas was insufficient and a storage stability was poor because of a high pH. Moreover, as in Comparative Example 3, in the case that sodium hydrogencarbonate was further added, the generation of the carbon dioxide gas was too large and the storage stability was also poor because of a low pH. In addition, in the case that calcium silicate was partially or additionally used in place of the activated carbon particles, the preparation of a powder was impossible (Comparative Example 4), and the oxygen absorbing performance was poor (Comparative Example 5).

On the other hand, the atmosphere regulators prepared in accordance with the present invention showed the good oxygen absorbing performance and carbon dioxide gas generation function without any unevenness of the performance, and the results of the storage stability were also excellent without any problem (Examples 1, 2 and 3).

Example 4

One platinum loopful of *Clostridium botulinum* (Sample bacteria No. 1) which grew as anaerobic bacteria in a GAM agar culture medium was suspended in 9 ml of a dilute solution for the anaerobic bacteria (hereinafter referred to as "the dilute solution") whose oxidation-reduction potential was lowered by adding L-cysteine or the like, and the suspension was further diluted to $10^4$ every 10 times to prepare dilute solutions. Two petri dishes containing the poured and solidified GAM agar culture medium were inoculated with 0.1 ml of each dilute solution to prepare culture plates. Next, two culture plates of each dilute solution and a package containing an atmosphere regulator in Example 1 were put in a bag of a gas barrier film (made of a polyvinylidene chloride-covered nylon-polyethylene) together with 2.5 liters of air, followed by sealing the bag up. Each gas barrier film bag was maintained at 37° C. for 3 days for the sake of the cultivation of the anaerobic bacteria, and the bag was opened and the number of colonies appeared on the agar culture medium and the diameters of the colonies were then measured.

A culture test of anaerobic bacteria was conducted by the same procedure as described above except that a culture medium was inoculated with *Bacteroides fragilis* (Sample bacteria No. 2) as the anaerobic bacteria and a package containing an atmosphere regulator in Example 1 was used as an atmosphere regulator. The results are shown in Table 8.

TABLE 8

|  | Sample Bacteria No. 1 | Sample Bacteria No. 2 |
| --- | --- | --- |
| Number of Colonies |  |  |
| Dilution Ratio ($10^3$) | 270, 239 | *, * |
| Dilution Ratio ($10^4$) | 31, 30 | 305, 311 |
| Diameter of Colonies | 8.8 mm | 2.8 mm |

*: The measurement was impossible (500 or more).

What is claimed is:

1. An atmosphere regulator consisting essentially of a powder of (a) 100 parts by weight of an oxygen absorber consisting essentially of activated carbon particles having an average particle diameter of 0.1 to 2 mm, an ascorbic acid compound, water and a metallic salt which is not a carbonate, or a hydrogen carbonate or a calcium silicate and (b) 5 to 20 parts by weight of alkaline earth metal hydroxide particles having an average particle diameter of 1 to 100 μm, the atmosphere regulator having a pH as measured in accordance with JIS K1474 being in the range of 10 to 12.5, the oxygen absorber being obtained by impregnating the activated carbon with the ascorbic acid compound, the metallic salt and water, and the atmosphere regulator being prepared by adding the alkaline earth metal hydroxide to the oxygen absorber thus obtained.

2. An atmosphere regulator package which is made by wrapping the atmosphere regulator described in claim 1 into a breathable package material.

3. A method for culturing anaerobic bacteria which comprises placing the atmosphere regulator described in claim 1 in a hermetically sealable container together with a culture medium inoculated with the anaerobic bacteria, and then hermetically sealing the container to regulate concentrations in the container atmosphere so that an oxygen concentration is 0.1% or less and a carbon dioxide gas concentration is in the range of 9 to 12% within 3 hours from the sealing of the container.

4. A method for culturing anaerobic bacteria which comprises placing the atmosphere regulator package described in claim 2 in a hermetically sealable container together with a culture medium inoculated with the anaerobic bacteria, and then hermetically sealing the container to regulate concentrations in the container atmosphere so that an oxygen concentration is 0.1% or less and a carbon dioxide gas concentration is in the range of 9 to 12% within 3 hours from the sealing of the container.

5. The atmosphere regulator according to claim 1 wherein the ascorbic acid compound is in an amount in the range of 20 to 200 parts by weight with respect to 100 parts by weight of the activated carbon.

6. The atmosphere regulator according to claim 1 wherein the particle diameter of the activated carbon is in the range of 0.2 to 1 mm.

7. The atmosphere regulator according to claim 1 wherein the metallic salt is in an amount in the range of 5 to 20 parts by weight with respect to 100 parts by weight of the ascorbic acid compound.

8. The atmosphere regulator according to claim 1 wherein the alkaline earth metal hydroxide is in a state of a powder having an average diameter of 2 to 50 μm.

9. The atmosphere regulator according to claim 5 wherein the ascorbic acid compound is selected from the group consisting of at least one of L-ascorbic acid, sodium L-ascorbate, calcium L-ascorbate and sodium D-isoascorbate; the metallic salt is selected from the group consisting of ferrous chloride, ferric chloride, ferric sulfate, manganese chloride, zinc sulfate, copper sulfate and copper chloride; the metallic salt is in an amount of 5 to 20 parts by weight with respect to 100 parts by weight of the ascorbic acid compound; the particle diameter of the activated carbon is 0.2 to 1 mm; the alkaline earth metal hydroxide is selected from the group consisting of at least one of calcium hydroxide and magnesium hydroxide; and the alkaline earth metal hydroxide has an average diameter of 2 to 50 μm.

10. A hermetically sealable container for culturing anaerobic bacteria, which comprises the atmosphere regulator described in claim 1 being disposed in the hermetically sealable container together with a culture medium inoculated with the anaerobic bacteria.

11. The hermetically sealable container for culturing anaerobic bacteria according to claim 10 wherein the concentrations of oxygen and carbon dioxide gas in the container are regulated so that the oxygen concentration is 0.1% or less and the carbon dioxide gas concentration is in the range of 9 to 12% within 3 hours from the sealing of the container.

12. A hermetically sealable container for culturing anaerobic bacteria, which comprises the atmosphere regulator package described in claim 2 being disposed in the hermetically sealable container together with a culture medium inoculated with the anaerobic bacteria.

13. The hermetically sealable container for culturing anaerobic bacteria according to claim 12 wherein the concentrations of oxygen and carbon dioxide gas in the container are regulated so that the oxygen concentration is 0.1% or less and the carbon dioxide gas concentration is in the range of 9 to 12% within 3 hours from the sealing of the container.

* * * * *